(12) United States Patent
Hartikainen et al.

(10) Patent No.: US 6,450,009 B1
(45) Date of Patent: Sep. 17, 2002

(54) METHOD AND DEVICE FOR MEASURING GAS PERMEABILITY THROUGH A POROUS MEMBRANE-LIKE MATERIAL

(76) Inventors: Juhani Hartikainen, Anttoninkatu 26 B 9, FIN-40250, Jyväskylä (FI); Kari Hartikainen, Anttoninkatu 11 as. 13, FIN-40250, Jyväskylä (FI)

( * ) Notice: Subject to any disclaimer, the term of this patent is extended or adjusted under 35 U.S.C. 154(b) by 0 days.

(21) Appl. No.: 09/647,628
(22) PCT Filed: Apr. 1, 1999
(86) PCT No.: PCT/FI99/00272
§ 371 (c)(1),
(2), (4) Date: Sep. 29, 2000
(87) PCT Pub. No.: WO99/50644
PCT Pub. Date: Oct. 7, 1999

(30) Foreign Application Priority Data

Apr. 1, 1998 (FI) .................................................. 980753
Jul. 29, 1998 (FI) .................................................. 981674

(51) Int. Cl.[7] ................................................ G01N 15/08
(52) U.S. Cl. .......................................................... 73/38
(58) Field of Search ............................................. 73/38

(56) References Cited

FOREIGN PATENT DOCUMENTS

DE         1063832      *   8/1959    ..................... 73/38

* cited by examiner

Primary Examiner—Daniel S. Larkin
(74) Attorney, Agent, or Firm—Fildes & Outland, P.C.

(57) ABSTRACT

A method and device for measuring gas permeability through a porous membrane-like material, particularly through paper where a sample is placed tightly against the edges of an open chamber, a gas connection is created to a source of constant pressure, a predetermined pressure difference is used to create a stable flow of gas through the sample, and at least one volume quantity is measured, which is proportional to the gas permeability of the material. The flow of gas is throttled before being led to the chamber, which rapidly stabilizes the flow.

12 Claims, 2 Drawing Sheets

METHOD AND DEVICE FOR MEASURING GAS PERMEABILITY THROUGH A POROUS MEMBRANE-LIKE MATERIAL

TECHNICAL FIELD

The present invention relates to a method and device for measuring gas permeability through a porous membrane-like material, in which method the volume flow rate through a sample is measured at a certain pressure. In addition to paper, the material may be various kinds of wires and felts. Measurements are performed by placing a sample against a chamber, after which a flow connection is made from the chamber to a source of constant pressure. The predetermined pressure-difference created by it is used to create a stable gas flow through the sample and the so-called volume flow rate is measured, this being proportional to the permeability of the material. The invention relates in particular to the investigation of membrane-like materials, such as greaseproof papers, which are only poorly permeable by gas.

BACKGROUND OF THE INVENTION

Methods and devices for measuring the gas permeability of a paper are known from patent publications U.S. Pat. No. 4,191,046, U.S. Pat. No. 4,462,248, UK 2 018 436, and UK 2 038 002. In these, the air permeability of a paper is measured by determining the average air flow permeating through a sample of a known surface area at a certain pressure difference. The known devices according to the patent publications are perfectly applicable to the measurement of air-permeable papers. In such devices, the volume flow rate is measured using either thermic flow meters, or with the aid of the pressure difference measured over a throttle.

All of the aforementioned patent publications are actually particularly intended for measuring the air permeability of cigarette papers. However, the reliable measurement of the grease-proofing of baking papers, for example, is not possible using the known devices referred to above, or else it is extremely difficult. The paper industry uses the so-called Linden method and measuring device to determine the air permeability of various paper materials. In this method, a standard quantity of compressed air is blown through a sample piece as a function of time. A corresponding method is also disclosed in publication U.S. Pat. No. 4,385,517. Particular problems in the measurement of poorly air-permeable materials, such as the greaseproof baking papers referred to above, are the poor repeatability of the results, and the slowness of the measurement. In addition, paper materials live with pressure, which makes it difficult to perform a repeatable measurement.

Devices according to the aforementioned patent publications give a stable result after a long waiting period, if even then. For example, a flow connection according to publication U.S. Pat. No. 4,191,046, used with a more sensitive flow sensor, behaves with an airtight sample in such a way that the volume flow rate displayed by the flow meter fluctuates over a considerable range. The problem does not appear when the volume flow rates are large, such as when measuring cigarette papers, which is, after all, the intended purpose of the device according to the publication. Measurement of the pressure difference over a throttle, disclosed in the other publications, is not suitable for low volume flow rates.

German patent publication DE 1 063 832, discloses an apparatus for measuring air permeability. In this device, there are three measurement zones, the smallest of which permits the measurement of the air permeability of even greaseproof papers. In the second and third measurement zones (II and III), a throttle (K2 or K3) is used to directly determine the volume flow rate created by a pressure difference. In the first measurement zone (I), a corresponding throttle is connected in the flow circuit after the sample and the pressure difference over the sample is measured, because the pressure difference over the throttle would be too small. In this case, the volume flow rate cannot be measured precisely. The arrangement is quite complicated and requires a sample-holder that is absolutely airtight on both sides of the sample.

It is wished to keep the surface area of the sample to a reasonable size, to be able to observe possible local variations in a sheet of paper.

SUMMARY OF THE INVENTION

The present invention is intended to create a new kind of method and device for measuring gas permeability through a porous membrane-like material, in particular dense paper. The invention is intended to avoid the problems of the state of the art. The characteristic features of the method according to the invention are disclosed in the accompanying claim 1. The characteristic features of a corresponding device are disclosed in the accompanying claim 8. The invention is largely based on the observation that the flow through the sample will stabilize very rapidly, if there is a throttle, preferably a long, narrow tube, in the flow duct, immediately before the sample. Even a small restriction has been shown to be advantageous. Other applications and advantages of the invention will appear in connection with the later embodiments.

In the following, the invention is described by reference to the accompanying figures, which show one measurement device according to the invention and its details.

DETAILED DESCRIPTION OF THE INVENTION

Figure 1:
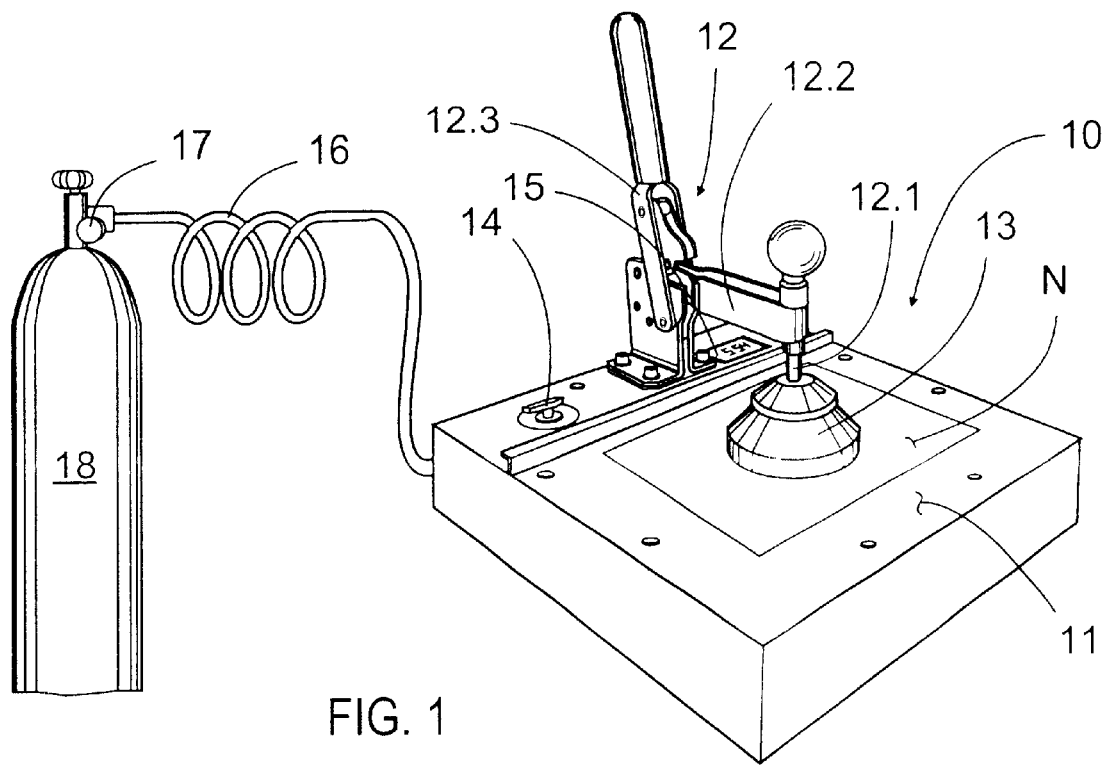
FIG. 1 shows the general arrangement of the measurement apparatus.
Figure 2:
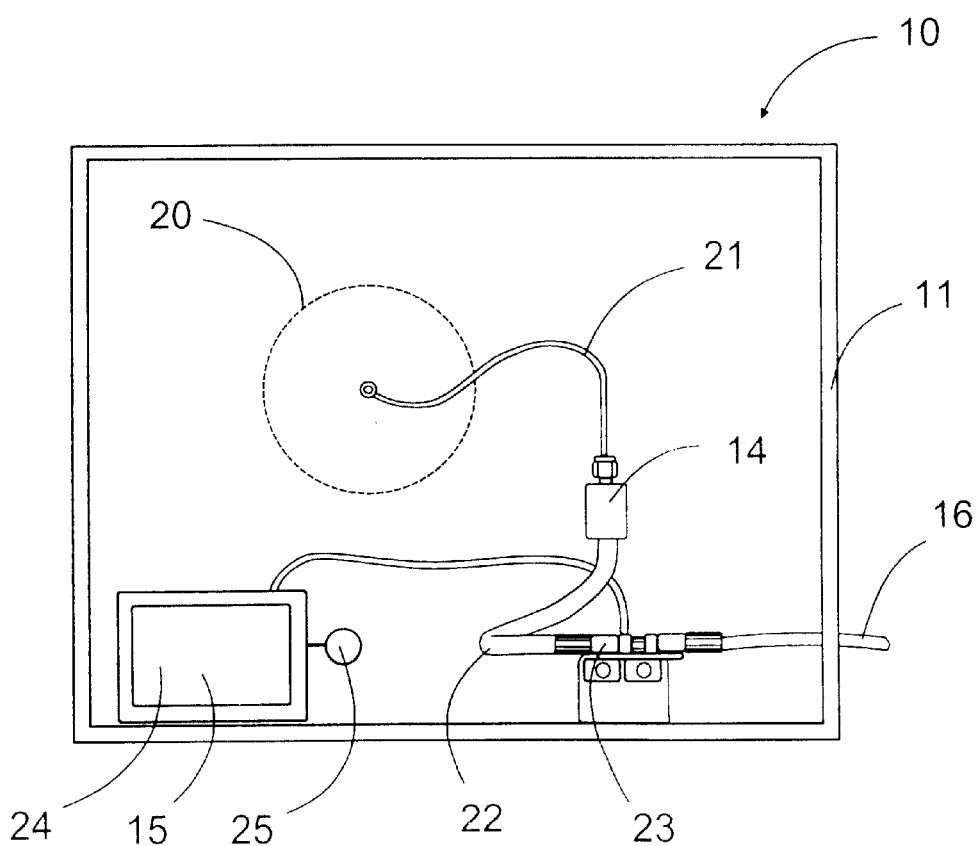
FIG. 2 shows the measurement device seen from below.

In FIG. 1, the measurement device is marked diagrammatically with the reference number 10. A high-pressure nitrogen bottle 18 is used as the source of gas, from which the gas is metered into the connection hose 16 through pressure control valve 17, and from there to measuring device 10. From the point of view of research, the connection hose 16 forms an essential free volume before the throttle point, due to which its length and internal diameter are precisely determined. There is a case 11 in the research device 10, in the upper part of which sample N is placed. The sample holder includes an upper chamber 13 and a press device 12. This comprises a press arm 12.1, a lever arm 12.2, and an operating handle 12.3. A shut-off valve handle 4 and a numerical display 15 are also located at the rear of the device.

Sample N is placed between the chamber 20 formed by the case 11 and the upper chamber 13. In practice, chamber 20 is formed by an O-ring protruding from the surface of case 11, to the centre of which the feed duct is connected.

Connection hose 16 is connected to flow meter 23, which is in turn connected to shut-off valve 14 by means of intermediate hose 22. From here, the gas is led by means of a narrow tube 21 through the case to the upper chamber 20 formed in the surface of the case. An electric signal is led from the flow meter 23 to an electronic unit 24, which controls a numerical display 15. Potentiometer 25 can be used to adjust the zero point, its button being arranged in the rear of the device, next to the numerical display.

Figure 3:
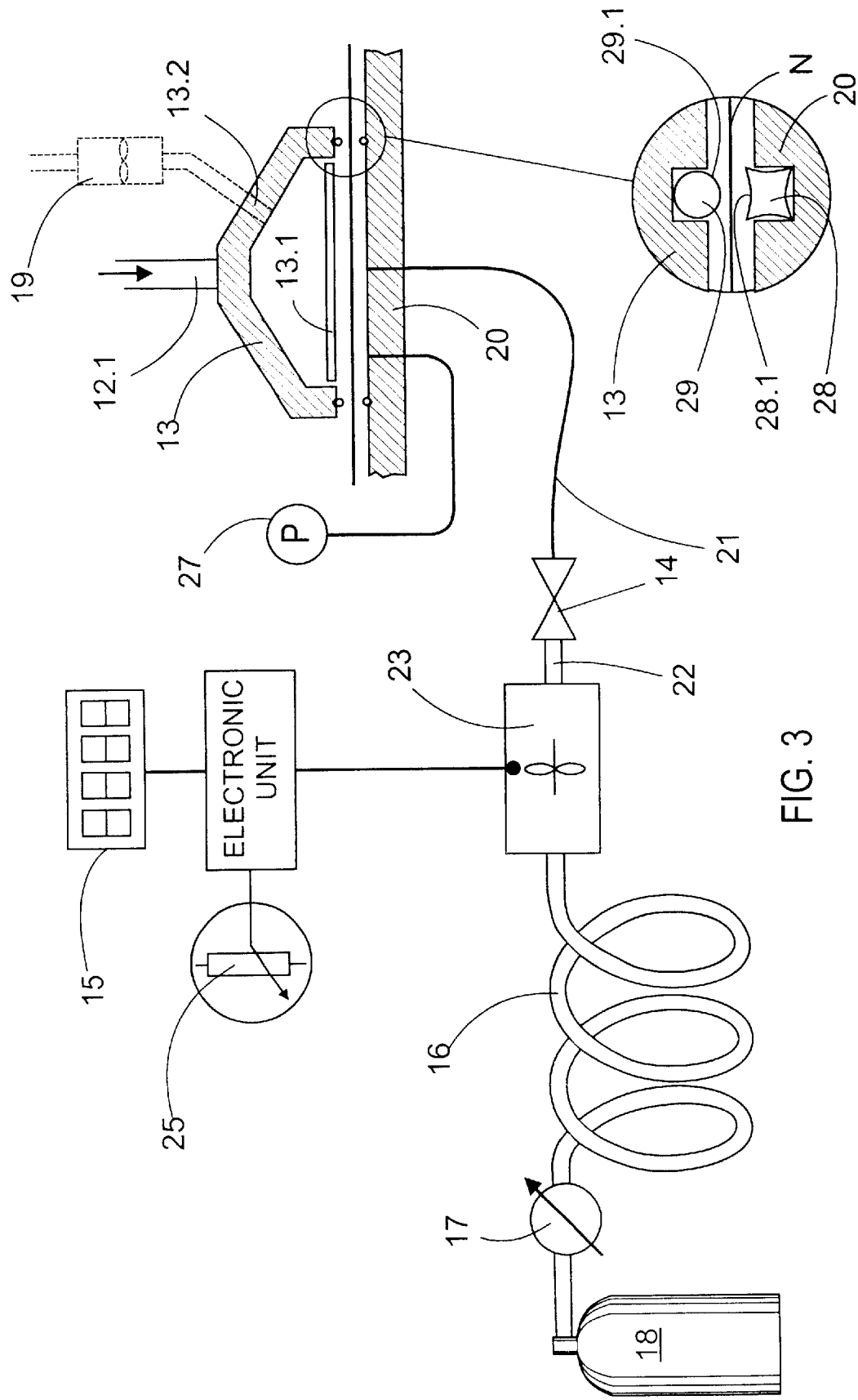
FIG. 3 shows a diagram of the measurement arrangement.

The operating principle of the device is shown in greater detail with the aid of FIG. 3. For a measurement, an essentially constant pressure is created by means of a source of constant pressure, which in this case comprises a nitrogen bottle 18 and a pressure regulating valve 17. With the aid of this, the pressure is adjusted to the desired level, typically a value of 200 mbar. The gas is led from the source of constant pressure to connection hose 16, which forms the large gas volume required in the measurement. Connected to the connection hose, there are, in order, as described above, a flow meter 23, an intermediate hose 22, a shut-off valve 14, and a flow throttling narrow tube 21, which leads the flow of gas to chamber 20.

The sealing of the sample in chamber 20 takes place by pressing the sample N against the seal of the edge of chamber 20, by means of the seal of the upper chamber 13. The paper is supported with the aid of a plate 13.1 that permits air to penetrate freely, for example a sinter plate, and the gas is led out through duct 13.2. This support 13.1 is absolutely necessary when investigating dense materials. During calibration, a connection from another flow meter 19 connected to the duct can be used.

In FIG. 3, chamber 20 and upper chamber 13 are shown separated from each other due to the requirements of the drawing, but during a measurement they are pressed tightly against each other. The detailed illustration shows the sealing mechanism, in which the sample is pressed between flexible ring seals 28 and 29, which are set in their own grooves in chambers 20 and 13. Preferably one, for example the counter-surface 28.1 of the lower seal 28 is concave or flat and correspondingly the counter-surface 29.1 of the opposite ring seal 29 is convex.

Flow meter 23 preferably uses thermic measurement, which is most suitable to low volume flow rates. The flow meter used can be, for example, the flow meter manufactured by Honeywell Inc. (USA), type AWM3100V. This has a volume flow rate range of 0–200 ml/min and an output of 1–5 V.

The flow meter data is read using an electronic unit 24. This also has connections for the remote transfer of measurements (not shown). For calibration of the device, the electronic unit includes a potentiometer 25, by means of which the reading shown on the numeric display 15 can be set as desired. The system is calibrated as follows. The numeric display is scaled to the range 1,000–5,000. Valve 14 is closed, when the numeric display can be calibrated to the value 1,000 by means of potentiometer 25. Next, the shut-off valve 14 is opened and, with the upper chamber 13 raised, i.e. in the full free flow position, the inlet pressure is set with the pressure regulator 17 so that the numerical display reads, for example, 5.50, which value is most advantageously close to the maximum capacity of the flow meter. After this, the chambers are connected without a sample and a known throttle, for example, a needle tube, which created one known calibration point, is connected to the outlet connection 13.2 of the upper chamber.

The absolute flow quantities are obtained with the aid of the electrical resistance values stated by the manufacturer of the flow meter, if these are generally required. The sample can now be placed supported by level plate 13.1 between the upper and lower chambers 20 and 13, and the flow led through the sample. The valve is kept open the whole time. If the volume flow is within the measurement range, the measurement value will stabilize rapidly.

If additional information is desired, the pressure in chamber 20 can be measured with a separate pressure meter 27 and the previously known methods used in addition.

One measuring device according to the invention uses 100 mm-diameter sealing rings, which define the surface area of the sample. The throttling flow channel 21, a capillary tube, has an internal diameter of 0.51 mm and a length of 300 mm. As a general instruction, the internal diameter can be given the value 0.3–0.9 and the length 150–500 mm. The connection hose is a flexible plastic hose with an internal diameter of 4 mm and a length of 5000 mm. The intermediate hose 22 is a 100 mm-long silicon hose.

When measuring greaseproof baking paper, the restriction of the throttling flow channel 21 in a state of equilibrium is only 0.1 per cent or less, measured from the total pressure drop from the source 18 of constant pressure through sample N, but the effect of the restriction when the measurement begins is even more important. Due to the restriction, the small chamber below the sample fills and the pressure rises with a delay. The volume flow then always and repeatably approaches from the same direction the final measurement value of the state of equilibrium. Because the pressure below the sample rises to a high value and attempts to inflate the sample, support plate 13.1 is essential to achieve a reliable measurement.

At the upper end of the measurement range, the restriction can be up to 90 per cent, calculated in a corresponding manner.

For example, a 300 mm-long capillary tube used as a throttle will achieve a delay of about 35 s in a flow of 105 $\mu$l/min, which was measured using one grade of greaseproof baking paper (reading 1,020).

The measurement range can be easily extended by using parallel flow meter circuits. In one embodiment, multi-way valves are used to select one channel out of several combinations of flow meter and throttle tube, in which each throttle tube is connected to the chamber. The flow meter and the throttle tube must be adapted to each other in such a way that the relative proportion of the restriction remains the same in different ranges.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. A method for measuring gas permeability through a porous material, in which method a sample is placed tightly against the edges of an open chamber, to which a gas connection is created to a source of constant pressure, using the predetermined pressure difference to create a stable flow of gas through the sample, and measuring the volume flow, which is proportional to the gas permeability of the material, characterized in that the flow of gas is throttled by being led to the chamber to create a delay in the rise in chamber pressure prior to commencing measurement.

2. A method according to claim 1, characterized in that the throttling is carried out using a long, thin tube compared to the free volume between the source of constant pressure and the beginning of the throttle.

3. A method according to claim 2, characterized in that, before the volume flow rate measurement, a large volume is used, which in turn is located before the aforesaid throttling of the flow.

4. A method according to claim 3, characterized in that the sample is supported on a low pressure side of a level.

5. A method according to claim 4, characterized in that airtight chambers are set on both sides of the sample and the volume flow rate is measured on both sides of the sample.

6. A method according to claim 5, characterized in that the pressure of the chamber is measured.

7. A method according to claim 1, characterized in that the volume flow rate is measured downstream of the sample.

8. A device for measuring gas permeability through a porous material, which device includes a flow duct with a sequentially connected pressure source, a pressure regulator, and a chamber equipped with sample holders, and at least one flow quantity meter, including a volume and/or pressure meter, so that a pressure created by the pressure source and the pressure regulator through the sample set against the chamber can be measured and observed as a quantity proportional to the permeability of the material, characterized in that before the chamber there is a flow-throttling flow duct, the volume of which is essentially smaller than the volume of the flow duct extending from the pressure regulator to the flow-throttling flow duct.

9. A device according to claim 8, in that the flow-throttling duct is formed by a thin tube, with an internal diameter of 0.3–0.9 mm and a length of 150–500 mm.

10. A device according to claim 9, characterized in that the chamber and the holders include ring seals that press the sample between them.

11. A device according to claim 10, characterized in that one ring seal has a concave counter-surface against the sample and the other ring seal has a corresponding convex or flat counter-surface.

12. A device according to claim 11, characterized in that the device includes a connection hose to the source of constant pressure, which forms a large volume relative to the volume of the rest of the flow circuit.

* * * * *